(12) United States Patent
Mitamura et al.

(10) Patent No.: US 6,437,506 B1
(45) Date of Patent: Aug. 20, 2002

(54) SOL SOLUTION AND METHOD FOR FILM FORMATION

(75) Inventors: Satoshi Mitamura; Toshio Yoshihara; Nobuko Takahashi, all of Tokyo-To (JP)

(73) Assignee: Dai Nippon Printing Co., Ltd. (JP)

( * ) Notice: Subject to any disclaimer, the term of this patent is extended or adjusted under 35 U.S.C. 154(b) by 0 days.

(21) Appl. No.: 09/653,587

(22) Filed: Aug. 31, 2000

Related U.S. Application Data

(62) Division of application No. 08/726,173, filed on Oct. 4, 1996, now Pat. No. 6,149,967.

(30) Foreign Application Priority Data

| Oct. 9, 1995 | (JP) | ............................................. 7-286326 |
| Oct. 9, 1995 | (JP) | ............................................. 7-286327 |
| May 23, 1996 | (JP) | ............................................. 8-150485 |

(51) Int. Cl.$^7$ .............................................. H01J 17/49
(52) U.S. Cl. ...................................... 313/586; 313/582
(58) Field of Search ................................. 313/582, 583, 313/584, 585, 586, 587; 427/66, 68, 380; 106/287.1, 287.16, 287.17, 287.19, 2

(56) References Cited

U.S. PATENT DOCUMENTS

| 1,955,211 A | 4/1934 | von Hoessle ................. 516/33 |
| 3,364,057 A | 1/1968 | Jackson ....................... 427/380 |
| 3,508,869 A | 4/1970 | Shoaff ......................... 423/639 |
| 3,847,583 A | 11/1974 | Dislich et al. ............... 427/380 |
| 3,850,683 A | 11/1974 | Hill .......................... 106/286.6 |
| 5,003,221 A | 3/1991 | Shimizu ....................... 427/66 |
| 5,510,141 A | 4/1996 | Makita et al. ............... 427/380 |

FOREIGN PATENT DOCUMENTS

| JP | 06325696 A | * 11/1994 | ................. 313/567 |

OTHER PUBLICATIONS

The Condensed Chemical Dictionary, 6$^{th}$ Edition, Edited by A. Rose et al., Reinhold Publ. Corp., New York, p. 1187 [QD 5 C5 1961 C. 38] 1961 (no month).

* cited by examiner

Primary Examiner—Vip Patel
Assistant Examiner—Joseph Williams
(74) Attorney, Agent, or Firm—Parkhurst & Wendel, L.L.P.

(57) ABSTRACT

A method for forming a protective layer for a dielectric material in an alternating current type plasma display is provided. In this connection, a coating sol solution is provided which can form a protective layer on a large area substrate without the need to introduce any expensive equipment, the protective layer thus formed being excellent in properties such as strength, adhesion, transparency, and protective properties and capable of being formed by a sol-gel process without use of the conventional vacuum process. The sol solution comprises a dispersion of a precursor to magnesium oxide in a specific form. A method for film formation, using this solution is also provided.

1 Claim, 3 Drawing Sheets

SOL SOLUTION AND METHOD FOR FILM FORMATION

This is a division of application Ser. No. 08/726,173 filed Oct. 4, 1996, now U.S. Pat. No. 6,149,967.

BACKGROUND OF THE INVENTION

The present invention relates to a sol solution and a method for film formation, and more particularly to a sol solution useful for the formation of a protective layer for a dielectric layer in an alternating current type plasma display and a method for film formation using the sol solution.

For optical components, electronic and electrical components, magnetic material components and the like, layers having various functions are formed on the substrate, and, if necessary, a protective film is provided on the surface of these layers for protection purposes. High film strength and large adhesion to the above functional layers are general properties required of such protective films.

In recent years, research and development of flat panel displays as an alternative to CRT have been energetically conducted. Among them, the so-called "plasma display" which utilizes luminous phenomenon accompanying discharge in a display is classified, according to the structure of the electrode (mainly ITO), roughly into a direct current type, wherein metallic electrodes are exposed to a discharge space, and an alternating current type wherein electrodes are covered with a dielectric layer. In the latter alternating current type plasma display, those produced by both a thin-film process using a vacuum system and a thick-film process using screen printing have begun to be put to practical use.

When the use of the plasma display in a color television with a large screen size is contemplated, the plasma display should have a memory function from the viewpoint of increasing the brightness. In this respect, the alternating current type plasma display inherently has a memory function by virtue of charges accumulated in the protective layer provided on the dielectric layer and, hence, is considered to be able to cope with a demand for an increase in screen size. Magnesium oxide having high secondary electron emission efficiency and excellent sputtering property has been used as a material for the protective layer. At the present time, a service life of 15000 hr. has been achieved for a full-color, alternating current type plasma display, and a panel having a diagonal distance of 21 in. has been put on the market.

Methods for forming the protective layer include thin-film processes, such as EB deposition, sputtering, and CVD (Japanese Patent Publication Nos. 42579/1985 and 59221/1988), and thick-film processes, such as one that comprises spray-coating basic magnesium carbonate as a starting material for magnesium oxide on a substrate to form a thick coating and firing the coating to convert the basic magnesium carbonate to a metal oxide (Japanese Patent Publication No. 13983/1982) and one that comprises dispersing a fine powder of magnesium oxide in a liquid binder which, upon firing, can be converted to an oxide, thereby forming a magnesium oxide film (Japanese Patent Publication No. 283020/1994).

Among the above methods, those using a vacuum process, such as EB deposition, sputtering, and CVD, are disadvantageous in that it is difficult to accommodate a large panel substrate, like a plasma display, in a vacuum chamber, posing problems of cost of equipment and productivity when an increased screen size is assumed.

Coating is a simple method and, hence, has been extensively and intensively studied in the art. At the present time, however, no satisfactory performance could have been attained yet. The reason for this unsatisfactory performance is as follows. In the coating, a magnesium oxide printing paste containing magnesium oxide particles is used for printing a magnesium oxide protective layer for alternative current type PDP. In order that the protective layer has sputtering resistance, magnesium oxide should be in the form of homogeneous particles having a diameter of 30 to 300 nm and, at the same time, the particles should be homogeneously dispersed in a binder. However, fine particles of magnesium oxide are likely to agglomerate and becomes very difficult to be homogeneously dispersed in the binder. For this reason, in the conventional commercially available printing paste, the diameter of incorporated magnesium oxide particles per se is large and the viscosity of the paste per se is high, making it difficult to reduce the thickness of the protective layer. Consequently, no highly even protective film can be formed. Further, the conventional printing paste is disadvantageous in that the conventional heat treatment process (600° C. or below) cannot offer satisfactory film strength, adhesion and other properties and heat treatment causes cracking of the film. The coatability of the paste is also unsatisfactory. Furthermore, the magnesium oxide particles incorporated are large, and the viscosity of the paste per se is high, making it difficult to reduce the layer thickness. This in turn poses a problem that a demand for minimized firing voltage and drive voltage cannot be met.

In order to solve the above problems involved in the coating method, the present inventors have previously proposed a method, using the so-called sol-gel process, that comprises the steps of: coating a magnesium hydroxide sol, prepared by hydrolyzing a magnesium oxide compound, onto a substrate; drying and firing the coating to form a magnesium oxide-containing thin film (Japanese Patent Laid-Open No. 111177/1996).

This method, however, is disadvantageous in that the adhesion of the magnesium hydroxide sol to the substrate is so poor that a part of the resultant magnesium oxide layer is easily separated from the substrate and the film thickness is uneven. Therefore, the above method is substantially ineffective in improving the firing voltage and the drive voltage (power consumption). Further, heat treatment of the magnesium hydroxide sol at a conventional temperature (600° C. or below) does not accelerate the crystallization of the resultant magnesium oxide. Therefore, the film thus obtained has a low crystallinity and, hence, unsatisfactory film strength, causing a problem that properties as a protective film cannot be satisfactorily exhibited.

On the other hand, the use of an organometallic compound, such as a magnesium alkoxide, as a starting compound for the magnesium hydroxide sol can offer magnesium oxide having relatively good adhesion to the substrate and uniformity in the film. Magnesium alkoxides and the like involve a problem of cost, because they are very expensive, and, in addition, a problem associated with handling because the reactivity of the magnesium alkoxides is so high that the control of the reaction is difficult and the life of the resultant magnesium hydroxide is short.

Under the above circumstances, the present invention has been made, and an object of the present invention is to solve the above problems of the prior art and to provide a sol solution that can form a film on a panel having a large area without the need to use expensive equipment such as required in the vacuum process, the formed film having excellent film strength, adhesion, transparent, protective properties and other properties and being usable as a protective layer that can lower the firing voltage and the drive voltage (power consumption), and to provide a method for film formation using said sol solution.

DISCLOSURE OF INVENTION

The first invention relates to a sol solution comprising a dispersion of fine particles of magnesium hydroxide bonded to a polyhydric alcohol or a derivative thereof in an organic solvent containing an organic compound having at least one hydroxyl group, and a method for film formation using said sol solution.

The second invention relates to a sol solution comprising a dispersion of an agglomerate of fine particles of magnesium hydroxide in an organic solvent containing at least one hydroxyl-containing organic compound, and a method for film formation using said sol solution.

The third invention relates to a sol solution comprising a dispersion of a partial or complete hydrate of magnesium acetate tetrahydrate as colloidal particles in a medium composed mainly of water, and a method for film formation using said sol solution.

According to the present invention, the formation of a protective layer, for example, in an alternating current type plasma display from the above specific sol solution realizes the formation of a film, as the protective layer, on a panel having a large area without the need to use expensive equipment such as required in the vacuum process, the formed film having excellent film strength, adhesion, transparent, protective properties and other film properties and being usable as a protective layer to provide an alternating current type plasma display that can lower the firing voltage and the drive voltage (power consumption).

BEST MODE FOR CARRYING OUT THE INVENTION

Figure 1:
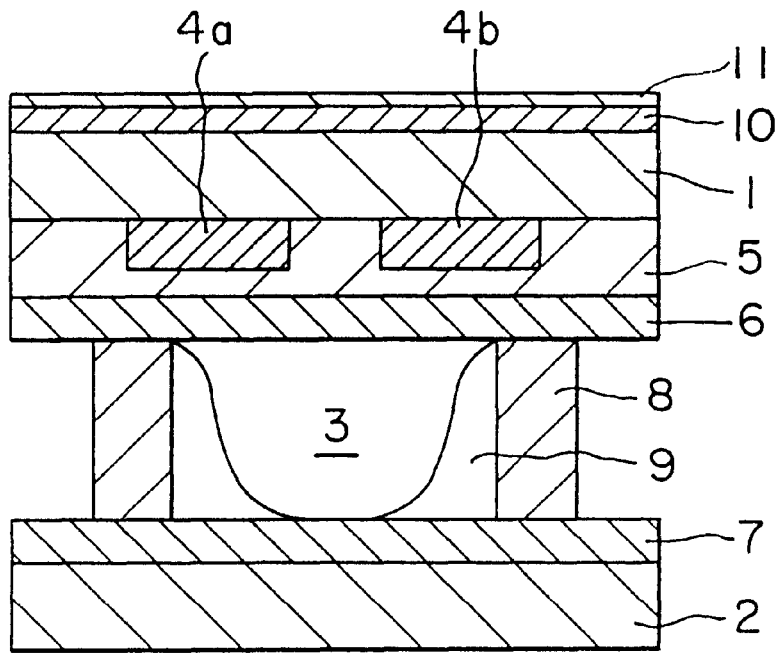
FIG. 1 is a schematic cross-sectional view of a plane discharge, alternating current type plasma display to which the sol solution according to the present invention has been applied.

The present invention will be described in more detail with reference to the following preferred embodiments.

First Invention

The sol solution according to the first invention comprises a dispersion of fine particles of magnesium hydroxide bonded to a polyhydric alcohol or a derivative thereof (fine particles of a double hydroxide of magnesium) in an organic compound having at least one hydroxyl group or an organic solvent containing said organic compound. The fine particles of the double hydroxide of magnesium may be produced by hydrolyzing a magnesium compound, convertible to magnesium hydroxide in the presence of water, in water and a polyhydric alcohol or a derivative thereof in the presence of a suitable catalyst to produce magnesium hydroxide and separating the particles from the reaction medium. The particles of the double hydroxide of magnesium thus obtained is considered to have such a structure that magnesium hydroxide and the polyhydric alcohol or derivative thereof are bonded to each other through a covalent bond, ionic bond, coordinate bond, or a hydrogen bond. That is, it is considered that a composite of magnesium hydroxide and the polyhydric alcohol or derivative thereof having an indefinite ratio is formed.

An embodiment of preparation of fine particles of double hydroxide of magnesium is as follows.

TABLE A1

Example of preparartion of fine particles of double hydroxide of magnesium

| | |
|---|---|
| Pure water | 50 parts by weight |
| Ethylene glycol | 150 parts by weight |
| Magnesium acetate (tetrahydrate) | 21 parts by weight |
| Aqueous ammonia (28 vol %) | 6 parts by weight |

Stirring of a mixed solution containing a composition as specified in Table A1 for one hr. at room temperature results in the formation of a double hydroxide of magnesium which is then separated from the medium by a suitable method to give fine particles of a double hydroxide of magnesium.

This is merely one embodiment, and, in general, any magnesium compound is usable so far as it can form magnesium hydroxide in the presence of water. The amount of the polyhydric alcohol or derivative thereof used is about 50 to 950 parts by weight based on 100 parts by weight of the magnesium compound, and the amount of water used is about 25 to 1500 parts by weight based on 100 parts by weight of the magnesium compound. The magnesium compound is hydrolyzed in the presence of a suitable catalyst. The catalyst may be any one so far as it can accelerate the hydrolysis of the magnesium compound. For example, when the magnesium compound is a magnesium salt, a basic compound is used, as the catalyst, in an amount of not less than one equivalent, preferably about 1 to 5 equivalents, based on one equivalent of the magnesium compound. When the catalyst is in the form of an aqueous solution, such as aqueous ammonia, the water contained in the aqueous ammonia solution can be used as water specified in the above table.

Magnesium compounds usable instead of the magnesium compound given in the table include, for example, magnesium salts of strong acids typified by magnesium chloride, magnesium nitrate, and magnesium sulfate, magnesium salts of weak acids typified by magnesium phosphate, magnesium hydrogenphosphate, magnesium dihydrogenphosphate, magnesium carbonate, magnesium citrate, magnesium hydrogencitrate, and magnesium formate, and magnesium salts of aliphatic carboxylic acids typified by magnesium stearate and magnesium myristate.

In Table A1, ethylene glycol, which forms fine particles of a double hydroxide of magnesium and serves also as a solvent, is one preferred example of the polyhydric alcohol or derivative thereof, and, for example, diethylene glycol, dihydric alcohols typified by 2-methoxyethanol, 2-ethoxyethanol, and triethylene glycol and derivatives thereof, trihydric or higher polyhydric alcohols typified by glycerin, mixture systems thereof, and organic solvents containing the above compounds, are usable instead of ethylene glycol.

Water as the solvent is an indispensable substance for the formation of fine particles of the double hydroxide of magnesium. However, it is needless to say that, in some cases, water need not be intentionally added on the premise that water contained in the aqueous ammonia is utilized.

Ammonia in the aqueous ammonia functions as a catalyst which accelerates the formation of magnesium hydroxide. Various ammonium salts typified by ammonium acetate, ammonium amidosulfate, ammonium carbonate, ammonium hydrogencarbonate, ammonium borate, diammonium citrate, ammonium dihydrogenphosphate, diammonium hydrogenphosphate, triammonium phosphate, ammonium formate, and ammonium tartrate, and amines typified by hydroxylamine, ethanolamine, and methanolamine are usable instead of this ammonia. The aqueous ammonia is particularly preferred from the viewpoint of attaining the object of the present invention because it is less likely to cause inclusion of impurities in the sol solution.

The double hydroxide of magnesium can be separated from the mixed solution containing the double hydroxide of magnesium by any method, and examples of methods usable herein include filtration, decantation, and centrifugation. A cooling/centrifuge (Model 7930, manufactured by Kubota Product Company Limited) was used in the separation of fine particles of the double hydroxide of magnesium produced from the composition specified in Table A1.

The fine particles of the double hydroxide of magnesium thus obtained is dispersed in an organic compound having at least one hydroxyl group or an organic solvent containing the above organic compound to prepare the sol solution of the present invention. The amount of the organic solvent used for the double hydroxide of magnesium may be suitably set. Since, however, the coating thickness is regulated by the set value of this parameter, this parameter should be carefully determined. For example, when the coatability of the resultant sol solution is taken into consideration, the organic solvent as the dispersing medium is preferably 100 to 500 parts by weight based on 100 parts by weight of the double hydroxide of magnesium. When the solid content is excessively low, it is difficult to form a dense, continuous protective layer, while when the solid content is excessively high, agglomeration precipitation of the fine particles of the double hydroxide of magnesium and a deterioration in uniformity of the protective layer are likely to occur. An embodiment of the sol solution is given in the following Table A2.

TABLE A2

Example of preparation of sol solution

| | |
|---|---|
| Double hydroxide of magnesium | 5 parts by weight |
| Ethanol | 10 parts by weight |

The double hydroxide can be dispersed by conventional dispersing means, such as simple stirring, forced stirring, ball mill, sand mill, and ultrasonic dispersion, and a homogeneous sol solution can be easily prepared by the above dispersing means. An ultrasonic device (MODEL US-300T, manufactured by NIHON SEIKi CO) was used in the dispersion of the composition specified in Table A2.

Ethanol is one example of the dispersing medium in the sol solution, and any compound may be used as the dispersing medium so far as it has at least one hydroxyl group. Dispersing media usable instead of ethanol include, for example, monohydric alcohols typified by methanol, n-propyl alcohol, i-propyl alcohol, 1-butanol, and 2-butanol, dihydric alcohols and derivatives thereof typified by ethylene glycol, diethylene glycol, 2-methoxyethanol, 2-ethoxyethanol, and triethylene glycol, trihydric or higher polyhydric alcohols typified by glycerin, and mixed solvents of these compounds or organic solvents containing at least one of the above organic solvents having at least one hydroxyl group.

In the present invention, the reason why the fine particles of the double hydroxide of magnesium can be easily dispersed in the above organic solvent by simple dispersing means is considered as follows.

Specifically, since the preparation of the fine particles of the double hydroxide of magnesium is carried out in a polyhydric alcohol or a derivative thereof, such as ethylene glycol, the polyhydric alcohol or derivative thereof is bonded or coordinated to each magnesium/aquo complex produced by hydrolysis, for example, by hydrogen bond to form a kind of chelate complex. As the hydrolysis proceeds through the action of the catalyst to increase the complex concentration, the chelate complexes associate with one another to form fine particles of the double hydroxide of magnesium. Since the formation of the fine particles (association of complexes) is carried out from a chelate complex of a polyhydric alcohol or a derivative thereof rather than from the magnesium/aquo complex, agglomeration of fine particles (agglomeration of complexes), which is likely to occur accompanying an increase in complex concentration, is reduced.

The fine particles, which are associated chelate complexes, when dispersed in a hydroxyl-containing organic solvent, cause the hydroxyl-containing organic solvent to adsorb to the fine particles through the hydroxyl group, so that a kind of protective film formed of the hydroxyl-containing organic solvent is formed on the surface of individual fine particles of the double hydroxide of magnesium. The presence of this protective film results in improved affinity of the fine particles for the organic solvent as a liquid medium for the sol solution and, at the same time, inhibits the agglomeration of fine particles in the organic solvent, permitting the fine particles to be easily and stably dispersed in the organic solvent. When this effect alone is taken into consideration, all organic compounds having a hydroxyl group are applicable. However, in order that, in the step of drying and firing after coating of the sol solution, the organic solvent is removed to prepare a film of pure magnesium oxide, it is preferred to use a polyhydric alcohol having a relatively low boiling point or a derivative thereof and to use an organic solvent having a relatively low boiling point as the solvent for the sol solution.

Figure 3:
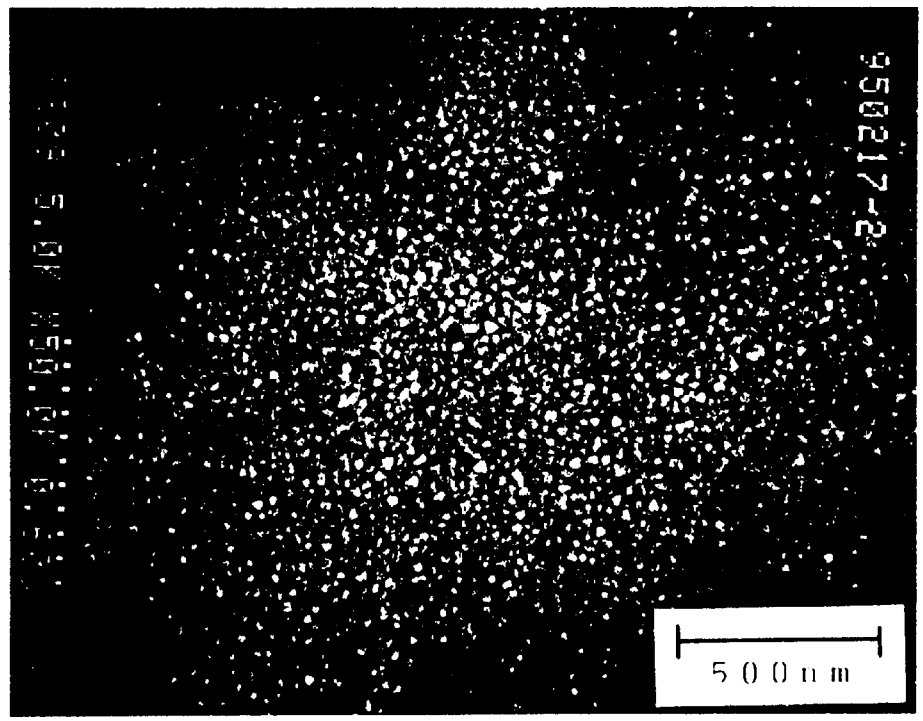
FIG. 3 is a scanning electron photomicrograph (magnification: 50000 times) showing the surface structure, in terms of particles, of a protective layer constituted by a magnesium oxide film prepared in Example A1.

The surface of a magnesium oxide film formed from a sol solution prepared without use of the polyhydric alcohol or derivative thereof in the preparation of magnesium hydroxide has irregularities having a size of about 200 nm, that is, large roughness, whereas, as shown in FIG. 3, the surface of a magnesium oxide film formed from a sol solution prepared using a polyhydric alcohol or a derivative thereof in the preparation of magnesium hydroxide has very small irregularities and is relatively even.

The reason why this phenomenon occurs is considered as follows. Specifically, for example, ethylene glycol is a solvent having a boiling point of 196° C., and, hence, an agglomerate of a magnesium hydroxide/ethylene glycol complex after centrifugation is viscous and creamy. On the other hand, magnesium hydroxide formed without using any polyhydric alcohol or derivative thereof is fundamentally an agglomerate of magnesium hydroxide alone, and, hence, the agglomerate after centrifugation is not very viscous. That is, in the case of the sol solution with ethylene glycol added thereto, it is considered that, upon coating of the sol solution, the effect of leveling by the agglomerate of fine particles is developed, rendering the surface of magnesium oxide after firing even as shown in FIG. 3.

Further, the fine particles of a double hydroxide of magnesium in the sol solution according to the present invention are a complex and, hence, less likely to associate with one another and less likely to agglomerate, as compared with fine particles of magnesium hydroxide prepared without using any polyhydric alcohol or derivative thereof. Therefore, the sol solution is stable even when the concentration of the sol solution is increased, which is advantageous in storage stability, coatability, and the steps of drying and firing.

Regarding the solvent for the sol solution, the use of water or a solvent not having any hydroxyl group, instead of the above alcoholic organic solvent, such as toluene or hexane, makes it difficult to stably disperse the fine particles of the double hydroxide of magnesium in the solvent, causing agglomeration and precipitation. For this reason, the organic solvent having a hydroxyl group, or an organic solvent containing at least one organic solvent of the above type is preferably used as the solvent for the sol solution.

Properties of sol solutions used in the present invention and Comparative Examples A1 and A2 described below are summarized, as experimental results supporting the above observation, in Table A3.

TABLE A3

Properties of various sol solutions

| Sample | Average particle size | Solid content | Stability with time |
|---|---|---|---|
| Ex. A1 | 836 nm | 18.5 wt % | Good |
| Comp. Ex. A1 | Immeasurable | 2.0 wt % | Poor |
| Comp. Ex. A2 | Immeasurable | 17.9 wt % | Poor |

The sol solution of Comparative Example A1 is one prepared by dispersing fine particles of magnesium hydroxide, prepared without adding ethylene glycol, in pure water instead of ethanol. The sol solution of Comparative Example A2 is one prepared by dispersing fine particles of a double hydroxide of magnesium in pure water instead of ethanol at the time of preparation of the sol solution.

Regarding the evaluation of the properties, the average particle size of the fine particles in the sol solution was measured and evaluated with a laser particle analyzer (PAR-III, manufactured by Otsuka Denshi K.K.) under conditions of pinhole φ 0.2. The solid content was determined by placing a given weight of each sol solution in a sample tube, drying the sample at 120° C. or 3 hr. and measuring the weight proportion of the residue. Regarding the stability with the time, upon the preparation of the sol solution, the sol solution was allowed to stand for one day to evaluate whether or not a precipitate occurred.

A method for film formation using the sol solution according to the present invention will be described with reference to the production of an alternating current type plasma display shown in the drawing by way of example.

DETAILED DESCRIPTION OF THE DRAWINGS

FIG. 1 is a schematic diagram showing the structure of a plane discharge, alternating current type plasma display according to a preferred embodiment of the present invention.

In FIG. 1, numerals 1 and 2 respectively designate a front substrate and a back substrate disposed parallel and opposite to each other with a gas discharge space 3 sandwiched therebetween. These front substrate 1 and back substrate 2 each are constituted by a glass sheet having a predetermined thickness.

A pair of electrodes, an electrode X 4a and an electrode Y 4b, are formed on the front substrate 1 in its surface facing the back substrate 2. These pair of electrodes are covered with a dielectric layer 5 made of glass, and the dielectric layer 5 is covered with a protective layer 6 constituted by a magnesium oxide film formed by coating the sol solution of the present invention and drying and firing the coating.

An address electrode 7, a barrier 8, and a phosphor layer 9 are formed on the back substrate 2 in its side facing the front substrate 1. Further, if necessary, for example, a titanium dioxide film (a high refractive index layer) 10 and a silicon dioxide film (a low refractive index layer) 11 are formed as a reflection preventive layer on the front substrate 1.

Figure 2:
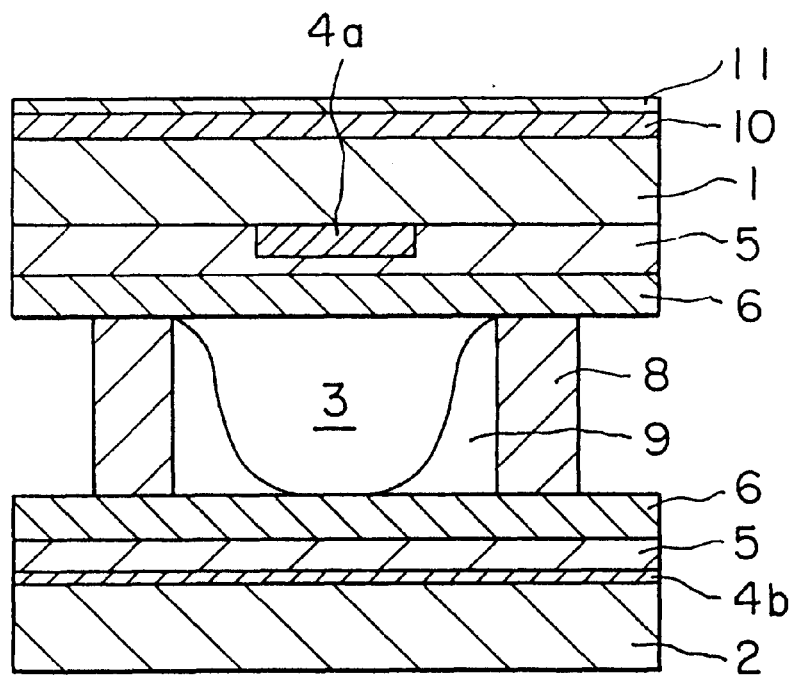
FIG. 2 is a schematic cross-sectional view of an opposed discharge, alternating current type plasma display to which the sol solution according to the present invention has been applied.

FIG. 2 is a schematic diagram showing the structure of an opposed discharge, alternating current type plasma display. In FIG. 2, an electrode X 4a is formed on the surface of a front substrate 1 in its surface facing a back substrate 2, the electrode X 4a is covered with a dielectric layer 5 made of glass, and the dielectric layer 5 is covered with a protective layer 6 formed of magnesium oxide prepared from a sol solution described below.

An electrode Y 4b, a dielectric layer 5, a protective layer 6 formed in the same manner as described above, and a barrier 8 and a phosphor 9 are provided on the back substrate 2 in its surface facing the front substrate 1.

Further, if necessary, for example, a titanium dioxide film (a high refractive index layer) 10 and a silicon dioxide film (a low refractive index layer) 11 are formed as a reflection preventive layer on the front substrate 1.

A process for producing an alternating current type plasma display according to the present invention is characterized by coating the above sol solution on the above dielectric layer and drying and firing the coating to form the above protective layer.

The sol solution may be coated on the dielectric layer by any coating method, and various coating methods, for example, spin coating, dip coating, spray coating, roll coating, meniscus coating, bar coating, curtain flow coating, bead coating, and casting, are applicable.

Drying and firing of a wet coating formed by the coating method result in the formation of a transparent magnesium oxide film as the protective layer, and the magnesium oxide film has high adhesion to the dielectric layer 5. The drying may be performed under conditions of such a temperature and a period of time that the organic solvent component in the wet coating is substantially removed by evaporation. For example, drying at a temperature of about 200 to 300° C. for about 1 to 3 hr. suffices for satisfactory results. Preferably, the firing can be performed at a temperature of about 350 to 550° C. for about 1 to 5 hr. Excessively severe firing conditions pose problems attributable to softening of the dielectric layer, such as delamination or cracking of the protective layer, On the other hand, when the firing is unsatisfactory, no protective layer having desired properties can be formed. Preferably, the drying and the firing are continuously performed. However, they may be separately performed. In a working example described below, the drying and the firing were continuously performed, that is, at 300° C. for one hr. and 400° C. for one hr.

Figure 4:
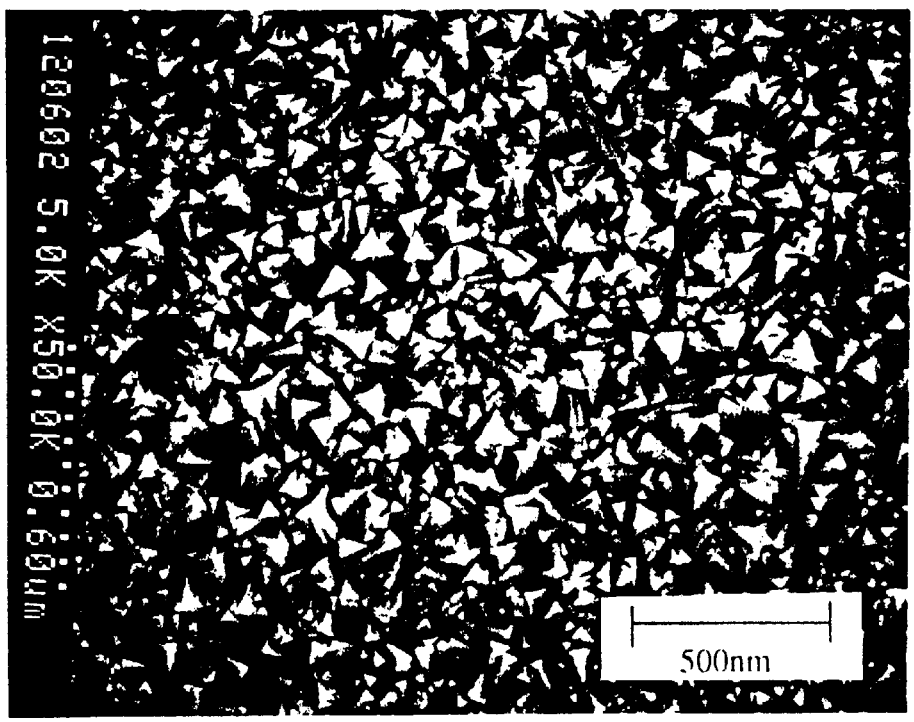
FIG. 4 is a scanning electron photomicrograph (magnification: 50000 times) showing the surface structure, in terms of particles, of a protective layer constituted by a magnesium oxide film formed by vacuum deposition in Comparative Examples A4 and B3.

In the present invention, a scanning type electron photomicrograph (magnification: 50000 times, device used: S-800, manufactured by Japan Electric Optical Laboratory) showing the surface structure, in terms of particles, of the protective layer constituted by a magnesium oxide film formed as described above is shown in FIG. 3. For comparison, a photomicrograph of the surface of a protective layer prepared by vacuum deposition in Comparative Example A4 described below is shown in FIG. 4. The measurement was conducted under conditions of accelerated voltage 5 kV, working distance 5 mm, beam monitor aperture No. 2, and objective movable aperture No. 3. As is apparent from FIG. 3, the protective layer constituted by the magnesium oxide film according to the present invention is such a dense, continuous film that the surface of the protective layer is constituted by particles, in a particulate form, having an average particle diameter of 30 nm. The form of the surface of the above film is clearly different from that of a magnesium oxide film, formed by vacuum deposition, constituted by flaky particles having an average particle diameter of 200 nm (FIG. 4).

In the present invention, the surface area of fine particles of magnesium oxide constituting the protective layer should be increased from the viewpoint of increasing the secondary electron emission ratio in the alternating current type plasma display, and, for this purpose, desirably, the diameter of fine particles of magnesium oxide is in the range of from 5 to 100 nm, preferably in the range of from 5 to 30 nm. The particle diameter is reduced to not more than 100 nm to reduce the gap between the particles and to enable an magnesium oxide film to be efficiently formed even by a conventional heat treatment process. Although the thickness of the magnesium oxide film is not particularly limited, it is preferably not more than 10 $\mu$m from the viewpoint of transparency, particularly preferably not more than 1 $\mu$m.

In the protective layer in the alternating current type plasma display thus obtained, a thin film having a thickness of not more than 1 $\mu$m can be realized, and such a film thickness cannot be realized by a paste using the conventional binder.

The sol solution according to the present invention can be used as a protective layer provided on the dielectric layer as a substrate in an alternating current type plasma display. Further, a magnesium oxide film can be formed on other substrates according to purposes.

Second Invention

The sol solution according to the second invention comprises a dispersion of an agglomerate of fine particles of magnesium hydroxide in an organic solvent containing at least one hydroxyl-containing organic compound. The agglomerate of fine particles of magnesium hydroxide may be produced by hydrolyzing a magnesium compound, convertible to magnesium hydroxide in the presence of water, in the presence of a suitable catalyst to produce magnesium hydroxide and separating the agglomerate from the reaction medium.

An embodiment of preparation of the agglomerate of fine particles of magnesium hydroxide is as follows.

TABLE B1

Example of preparation of fine particles of magnesium hydroxide

| | |
|---|---|
| Pure water | 200 parts by weight |
| Magnesium acetate (tetrahydrate) | 21 parts by weight |
| Aqueous ammonia (28 vol %) | 6 parts by weight |

Stirring of a mixed solution containing a composition as specified in Table B1 for one hr. at room temperature results in the formation of a precipitate of an agglomerate of fine particles of magnesium hydroxide which is then separated from water as the reaction medium by a suitable method to give an agglomerate of fine particles of magnesium hydroxide.

This is merely one embodiment, and, in general, any magnesium compound is usable so far as it can form magnesium hydroxide in the presence of water. The catalyst may be any one so far as it can accelerate the hydrolysis of the magnesium compound. For example, when the magnesium compound is a magnesium salt, a basic compound is used, as the catalyst, in an amount of not less than one equivalent, preferably about 1 to 5 equivalents, based on one equivalent of the magnesium compound. When the catalyst is in the form of an aqueous solution, such as aqueous ammonia, the water contained in the aqueous ammonia solution can be used as water specified in the above table.

Magnesium compounds usable herein include those exemplified above in connection with the first invention.

Ammonia in the aqueous ammonia functions as a catalyst which accelerates the formation of magnesium hydroxide. Various ammonium salts typified by ammonium acetate, ammonium amidosulfate, ammonium carbonate, ammonium hydrogencarbonate, ammonium borate, diammonium citrate, ammonium dihydrogenphosphate, diammonium hydrogenphosphate, triammonium phosphate, ammonium formate, and ammonium tartrate, and amines typified by hydroxylamine, ethanolamine, and methanolamine are usable instead of this ammonia. The aqueous ammonia is particularly preferred from the viewpoint of attaining the object of the present invention because it is less likely to cause inclusion of impurities in the sol solution.

The agglomerate of fine particles of magnesium hydroxide can be separated from the mixed solution containing the precipitate of an agglomerate of fine particle of magnesium hydroxide by any method, and examples of methods usable herein include filtration, decantation, and centrifugation. A cooling/centrifuge (Model 7930, manufactured by Kubota Product Company Limited) was used to in the separation of the agglomerate of fine particles of magnesium hydroxide produced from the composition specified in Table B1.

The fine particles of the agglomerate of magnesium hydroxide thus obtained is dispersed in an organic solvent containing at least one hydroxyl-containing organic compound to prepare the sol solution of the present invention. The amount of the organic solvent used for dispersing the agglomerate of fine particle of magnesium hydroxide may be suitably set. Since, however, the coating thickness is regulated by the set value of this parameter, this parameter should be carefully determined. For example, when the coatability of the resultant sol solution is taken into consideration, the organic solvent as the dispersing medium is preferably 100 to 1500 parts by weight based on 100 parts by weight of the fine particles of magnesium hydroxide. When the solid content is excessively low, it is difficult to form a dense, continuous protective layer, while when the solid content is excessively high, agglomeration precipitation of the fine particles and a deterioration in uniformity of the protective layer are likely to occur. An embodiment of the sol solution is given in the following Table B2.

TABLE B2

Example of preparation of sol solution

| Agglomerate of fine particles of magnesium hydroxide | 1 part by weight |
|---|---|
| Ethanol | 10 parts by weight |

The agglomerate can be dispersed by conventional dispersing means, such as simple stirring, forced stirring, ball mill, sand mill, and ultrasonic dispersion, and a homogeneous sol solution can be easily prepared by the above dispersing means. An ultrasonic device (MODEL US-300T, manufactured by NIHON SEIKi CO) was used in the dispersion of the composition specified in Table B2.

Ethanol is one example of the dispersing medium in the sol solution, and any organic compound having at least one hydroxyl group or any organic solvent containing at least one compound of the above type may be used as the dispersing medium. Dispersing media usable instead of ethanol include, for example, monohydric alcohols typified by methanol, n-propyl alcohol, i-propyl alcohol, 1-butanol, and 2-butanol, dihydric alcohols and derivatives thereof typified by ethylene glycol, diethylene glycol, 2-methoxyethanol, 2-ethoxyethanol, and triethylene glycol, trihydric or higher polyhydric alcohols typified by glycerin, aromatic compounds, such as phenol and cresol, and mixed solvents of these compounds or organic solvents containing at least one of the above organic solvents having at least one hydroxyl group.

In the present invention, the reason why the agglomerate of fine particles of magnesium hydroxide can be easily dispersed in the above organic solvent by simple dispersing means is considered as follows.

Specifically, when an agglomerate of fine particles of magnesium hydroxide is dispersed in a hydroxyl-containing organic solvent, the hydroxyl-containing organic solvent is bonded, coordinated, or adsorbed to an agglomerate (secondary agglomerate) of individual fine particles of magnesium hydroxide by taking advantage of the hydroxyl group through a hydrogen bond or the like to form fine particles covered with a kind of a protective film of the hydroxyl-containing organic solvent formed on the surface of the particles. It is considered that the presence of this protective film results in improved affinity of the fine particles for the organic solvent as a dispersing medium for the sol solution and, at the same time, inhibits the agglomeration of fine particles per se in the organic solvent, permitting the fine particles to be easily and stably dispersed in the organic solvent. When this effect alone is taken into consideration, all organic compounds having a hydroxyl group are applicable. However, in order that, in the step of drying and firing after coating of the sol solution, the organic solvent is removed to prepare a film of pure magnesium oxide, it is preferred to use a hydroxyl-containing organic solvent having a relatively low boiling point as the solvent for the sol solution.

Regarding the solvent for the sol solution, the use of water or a solvent not having any hydroxyl group, such as toluene or hexane, instead of the above alcoholic organic solvent, makes it difficult to stably disperse the fine particles of magnesium hydroxide in the solvent, causing agglomeration and precipitation. For this reason, the organic solvent having a hydroxyl group, or an organic solvent containing at least one organic solvent of the above type is preferably used as the solvent for the sol solution.

Properties of sol solutions used in the present invention and Comparative Example B1 described below are summarized, as experimental results supporting the above observation, in Table B3.

TABLE B3

Properties of various sol solutions

| Sample | Average particle size | Solid content | Stability with time |
|---|---|---|---|
| Ex. B1 | 873 nm | 0.9 wt % | Good |
| Comp. EX. B1 | Immeasurable | 2.0 wt % | Poor |

The sol solution of Comparative Example B1 is one prepared by dispersing an agglomerate of fine particles of magnesium hydroxide specified in Table B1, prepared without adding ethylene glycol, in pure water instead of ethanol.

Properties of the sol solutions were evaluated in the same manner as in the first invention.

A film can be formed using the sol solution according to the second, invention in the same manner as described above in connection with an embodiment of the production of alternating current type plasma displays, according to the present invention, shown in FIGS. 1 and 2.

Figure 5:
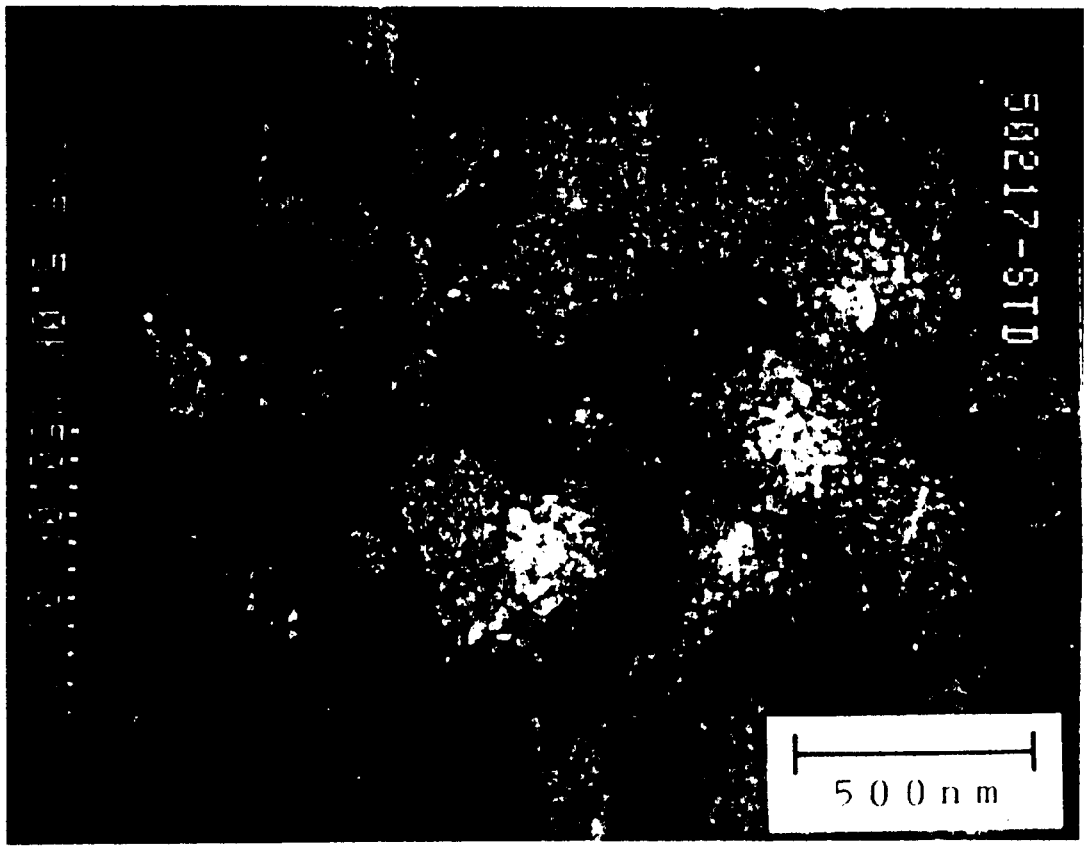
FIG. 5 is a scanning electron photomicrograph (magnification: 50000 times) showing the surface structure, in terms of fine particles, of a protective layer constituted by a magnesium oxide film prepared in Example B1.

In the present invention, a scanning type electron photomicrograph (magnification: 50000 times, device used: S-800, manufactured by Japan Electric Optical Laboratory) showing the surface structure, in terms of particles, of the protective layer constituted by a magnesium oxide film formed as described above is shown in FIG. 5. For comparison, a photomicrograph of the surface of a protective layer prepared by vacuum deposition in Comparative Example B3 described below is shown in FIG. 4. The measurement was conducted under conditions of accelerated voltage 5 kV, working distance 5 mm, beam monitor aperture No. 2, and objective movable aperture No. 3. As is apparent from FIG. 5, the protective layer constituted by the magnesium oxide film according to the present invention is such a dense, continuous film that the surface of the protective layer is constituted by particles, in a particulate form, having an average particle diameter of 30 nm. The form of the surface of the above film is clearly different from that of a magnesium oxide film, formed by vacuum deposition, constituted by flaky particles having an average particle diameter of 200 nm (FIG. 4).

In the present invention, the surface area of fine particles of magnesium oxide constituting the protective layer should be increased from the viewpoint of increasing the secondary electron emission ratio in the alternating current type plasma display, and, for this purpose, desirably, the diameter of fine particles of magnesium oxide is in the range of from 5 to 100 nm, preferably in the range of from 5 to 30 nm. The particle diameter is reduced to not more than 100 nm to reduce the gap between the particles, thereby increasing the surface area, and to enable an magnesium oxide film to be efficiently formed even by a conventional heat treatment process. Although the thickness of the magnesium oxide film is not particularly limited, it is preferably not more than 10 $\mu$m from the viewpoint of transparency, particularly preferably not more than 1 μm.

In the protective layer in the alternating current type plasma display thus obtained, a thin film having a thickness of not more than 1 μm can be realized, and such a film thickness cannot be realized by a paste using the conventional binder.

The sol solution according to the present invention can be used as a protective layer provided on the dielectric layer as a substrate in an alternating current type plasma display. Further, a magnesium oxide film can be formed on other substrates according to purposes.

Third Invention

The use of an organometallic compound, such as a magnesium alkoxide, as a starting compound for the magnesium hydroxide sol can offer magnesium oxide having relatively good adhesion to the substrate and uniformity in the film. Magnesium alkoxides and the like, however, involve a problem of cost because they are relatively expensive. Further, since the reactivity of the magnesium alkoxides is relatively high, the reaction should be carefully controlled. Furthermore, the life of the resultant magnesium hydroxide is so short that careful handling is necessary.

For the above reason, in general, an organometallic salt, such as magnesium acetate, or an inorganic metal salt, such as magnesium chloride or magnesium sulfate, is used instead of the magnesium alkoxide and the like. However, the use of a large amount of an alkali, such as ammonia, is necessary to prepare a magnesium hydroxide sol, requiring the step of removal of the alkali and the like. This often renders the production process complicated. Bringing the particle diameter to not more than 1 μm is preferred from the viewpoints of improving the transparency of the magnesium oxide layer and the adhesion of magnesium hydroxide to the substrate. For attaining this purpose, the addition of an additive, such as ethylene glycol, to the magnesium hydroxide sol production system is recommended from the viewpoint of inhibiting the growth of the particles. The addition of the above additive often inhibits the production of the magnesium hydroxide sol per se, resulting in lowered yield of the sol.

According to the third invention, when a sol solution of colloidal particles of magnesium acetate is used, for example, in the formation of a protective layer in an alternating current type PDP, a film can be formed on a panel having a large area without the need to use expensive equipment such as required in the vacuum process. The film thus formed has film strength, adhesion, transparent, protective properties and other film properties, and the of such a film enables the production of an alternating current type PDP that can lower the firing voltage and the drive voltage (power consumption).

The third invention is based on the present inventor's finding, that is, such finding that although a commercially available magnesium acetate is generally in tetrahydrate form and is completely soluble in water, partially dehydrated hydrous magnesium acetate and anhydrous magnesium acetate produced by partially or completely removing the water of hydration is insoluble in water and that the addition of the above magnesium acetate to water causes a part of the surface of particles to undergo hydrolysis to form hydrophilic magnesium hydroxide which is dispersed as stable colloidal particles in water.

The starting compound for forming the magnesium acetate sol according to the present invention is magnesium acetate tetrahydrate, and the removal of 20% by weight of the water of hydration is preferred from the viewpoint of forming stable colloidal particles in a medium composed mainly of water. Particularly preferably, the magnesium acetate is completely dehydrated to form anhydrous magnesium acetate. The dehydration may be performed by any method without limitation. For example, heating under reduced pressure is simple and, hence, is preferred.

The medium for dispersing the anhydrous or partially dehydrated magnesium acetate is composed mainly of water, that is, 100% water or a mixed solution of water and a water-soluble solvent. In particular, the use of alcohols, glycols, esters, ethers, or organic solvents having a high dielectric constant, such as propylene carbonate and γ-butyrolactone, are preferred from the viewpoint of allowing the hydrolysis of at least part of magnesium acetate on the surface of the particles to homogeneously and efficiently proceed, thereby forming a stable sol solution. The amount of the above organic solvent added to water is not particularly limited so far as the proportion of water in the mixed solution is not 50% by weight or less. The content (solid basis) of the anhydrous or partially hydrated magnesium acetate in the medium composed mainly of water is usually 0.1 to 90% by weight. However, it is preferably in the range of from 0.1 to 60% by weight from the viewpoint of forming a homogeneous sol solution.

A dispersion stabilizer may be incorporated into the sol solution in order to enhance the stability of the sol solution. Examples of preferred dispersion stabilizers include water-soluble polymers, for example, celluloses, such as hydroxypropyl methylcellulose and hydroxypropylmethyl cellulose, acrylic polymers, such as polyacrylic acid and polyacrylamide, and vinyl polymers, such as polyvinyl alcohol and a partially saponified product thereof. They may be used alone or a mixture of two or more, and the content of the dispersion stabilizer in the sol solution is usually in the range of from 0.01 to 10% by weight.

The sol solution containing magnesium acetate particles dispersed in a colloidal form can be prepared by adding anhydrous or partially hydrated magnesium acetate to medium composed mainly of water with a water-soluble solvent and a dispersion stabilizer being optionally dissolved therein and stirring the mixture. A reaction for forming the colloid smoothly proceeds at room temperature. However, heating to, for example, 30 to 80° C. can accelerate the reaction.

Further, in order to regulate the diameter of colloidal particles in a predetermined range, ethylene glycol or a derivative of ethylene glycol, such as diethylene glycol or methyl CELLOSOLVE® (2-ethoxyethanol), may be added to the above reaction system. The amount of ethylene glycol or a derivative thereof added is usually in the range of from 0.01 to 80% by weight. As the amount of ethylene glycol or a derivative thereof added increases, the diameter of colloidal particles decreases. The particle diameter distribution can be broadened or narrowed to give particles having uniform diameter, according to the purpose of use (application) of the sol solution of the present invention.

Therefore, for example, a sol solution containing a mixture of large colloidal particles with small colloidal particles may be used to form a dense magnesium oxide layer (film), or alternatively a sol solution containing colloidal particles having uniform diameter may be used to form a thin layer of magnesium oxide.

The reason why the diameter of the sol particles can be regulated is believed to reside in that an oxygen atom within the molecule of ethylene glycol or a derivative thereof is coordinated to the magnesium atom of magnesium acetate to stabilize the dispersibility of colloidal particles of magnesium acetate. In the sol solution of the present invention, the diameter of the colloidal particles is in the range of from 3 to 300 nm.

In the magnesium acetate sol solution according to the present invention, at least a part of magnesium acetate on the surface of the colloidal particles undergoes hydrolysis to form a magnesium hydroxide, rendering the sol solution stable. Further, when the magnesium acetate sol solution of the present invention is coated on a substrate to form a film, as compared with a film formed using a conventional coating liquid with magnesium hydroxide forcibly formed by adding aqueous ammonia to a magnesium acetate solution, the adhesion between the colloidal particle layer (film) and the substrate is significantly improved realizing a dense magnesium oxide layer having uniform particle diameter or the like.

The method for film formation according to the present invention comprises the steps of: coating the above magnesium acetate sol solution on a substrate; drying the resultant magnesium acetate film; and heat-treating the dried magnesium acetate film to form a magnesium oxide film.

The sol solution may be coated on the substrate by any coating method, and various coating methods, for example, spin coating, dip coating, spray coating, roll coating, meniscus coating, and bar coating, are applicable.

Drying and heat treatment (firing) of a wet coating formed by the coating method result in the formation of a transparent magnesium oxide film adhered to the substrate. The drying may be performed under conditions of such a temperature and a period of time that the water and the water-soluble solvent in the wet coating is substantially removed by evaporation. For example, drying at a temperature of about 100 to 200° C. for about 1 to 2 hr. suffices for satisfactory results. Preferably, the firing can be performed at a temperature of about 300 to 600° C. for about 1 to 5 hr. The heat treatment at the above temperature is preferred from the viewpoint of completely converting the magnesium hydroxide to magnesium oxide by firing and enhancing the crystallinity of the film to improve the film properties.

In the present invention, the surface area of fine particles of magnesium oxide constituting the protective layer should be increased from the viewpoint of increasing the secondary electron emission ratio in the alternating current type PDP, and, for this purpose, desirably, the diameter of fine particles of magnesium oxide is in the range of from 5 to 100 nm, preferably in the range of from 5 to 30 nm. The particle diameter is reduced to not more than 100 nm to reduce the gap between the particles, thereby increasing the surface area, and to enable an magnesium oxide film to be efficiently formed even by a conventional heat treatment process. Although the thickness of the magnesium oxide film is not particularly limited, it is preferably not more than 10 μm from the viewpoint of transparency, particularly preferably not more than 1 μm.

According to the magnesium oxide film prepared by the method of the present invention, a thin film, having a thickness of not more than 1 μm, of magnesium oxide alone can be produced without the use of any binder. The production of the above thin film has been unattainable by using the conventional magnesium oxide printing paste.

The formation of a protective layer having a thickness of not more than 2 μm in the case of, for example, an alternating current PDP is regarded as the most important necessary and sufficient condition from the practical viewpoint. The film formed by the method for film formation according to the present invention is formed in a thickness of not more than 1 μm and, hence, is particularly suitable as a protective layer (film) for a dielectric layer in the alternating current type PDP. The application of the film is not limited to this only.

EXAMPLE A1

An opposed discharge alternating current type plasma display shown in FIG. 2 was prepared as follows. A 0.2 μm-thick electrode X 4a as a chromium electrode was vacuum-deposited on a front substrate 1 made of glass. A 0.8 μm-thick dielectric layer 5 was then vacuum-deposited, and a sol solution specified in Table 2 was used to form a 0.2 μm-thick protective layer 6 of a magnesium oxide film on the dielectric layer 5. Thereafter, a 150 μm-thick barrier 8 was formed on the protective layer 6 by screen printing, and a fluorescent material was coated on the barrier 8 to form a 10 μm-thick phosphor layer 9.

Separately, a chromium electrode was vacuum-deposited on a back substrate 2 made of glass and patterned to form an electrode Y 4b, and a dielectric layer 5 was vacuum-deposited on the electrode Y 4b. Thereafter, a 0.2 μm-thick protective layer 6 of a magnesium oxide film was formed in the same manner as described above in connection with the magnesium oxide film. The film thickness of the chromium electrode (electrode Y 4b) on the back substrate 2 was 0.2 μm, and the film thickness of the dielectric layer 5 was 0.8 μm.

Both the substrates thus obtained were laminated to each other so that the protective layers faced each other. 500 Torr of He—Xe (1.1%) Penning gas was sealed into a space defined by the barrier 8 to prepare an opposed discharge alternating current type plasma display of the present invention.

COMPARATIVE EXAMPLE A1

An attempt to prepare an opposed discharge alternating current type plasma display was made in the same manner as in the above example, except that, in the preparation of fine particles of magnesium oxide, a sol solution prepared by dispersing fine particles of magnesium hydroxide, prepared without the addition of ethylene glycol, in pure water instead of ethanol, was used instead of the sol solution in the above example.

COMPARATIVE EXAMPLE A2

An attempt to prepare an opposed discharge alternating current type plasma display was made in the same manner as in the above example, except that, in the preparation of the sol solution, fine particles of a double hydroxide of magnesium were dispersed in pure water instead of ethanol.

COMPARATIVE EXAMPLE A3

An opposed discharge alternating current type plasma display was prepared in the same manner as in the above example, except that a paste of magnesium oxide was coated by screen printing to form the protective layer 6 of a magnesium oxide film. The paste of magnesium oxide was prepared by dispersing a magnesium oxide powder having an average primary particle diameter of 0.18 to 0.25 μm (UBE 2000A, manufactured by Ube Industries, Ltd.) in a Si-based binder (10 parts by weight of $SiO_2$) to a concentration of 26% by weight and modifying the viscosity to 7,000 cps/25° C.

Printing was performed under conditions of plate gap 2.3 mm, squeegee indentation 1 mm, scraper indentation 1 μm, screen mesh 400, and emulsion thickness 10 μm. Sintering was performed under atmospheric pressure at a temperature of 580° C. for one hr.

COMPARATIVE EXAMPLE A4

An opposed discharge alternating current type plasma display was prepared in the same manner as in the above example, except that the protective layer 6 of a magnesium oxide film was formed by vacuum deposition. In the vacuum deposition, an electron beam depositing machine (EX-900-C16, manufactured by Ulvac Japan Limited) was used to form a film under conditions of substrate temperature 300° C. and film formation rate 0.5 nm/sec to a thickness of 0.5 μm.

Before paneling, the alternating current type plasma displays (hereinafter referred to as "panels") prepared in the example and the comparative examples were evaluated for the properties of the magnesium oxide film constituting the protective layer. The results are summarized in Table A4. The adhesion and the film strength given in the table were evaluated by a scratch tester and a pencil hardness test. The transparency and the crack were visually inspected. The film thickness was measured with a profilometer (αStep 300, manufactured by Tencor Instruments Japan Co., Ltd.).

taining voltage was measured and compared with the initial minimum maintaining voltage to investigate a change in voltage with the elapse of time. Thus, the life property of the panels was evaluated. The results are summarized in Table A5.

TABLE A5

PDP properties ot various magnesium oxide films

| Sample | Firing voltage | Minimum maintaining voltage | Life |
| --- | --- | --- | --- |
| Ex. A1 | 155 V | 110 V | Good |
| Comp. Ex. A3 | 240 V | 175 V | Somewhat poor |
| Comp. Ex. A4 | 160 V | 105 V | Good |

As is apparent from Table A5, for the panel prepared in the example of the present invention, the firing voltage was 155 V, the minimum maintaining voltage was 110 V, and no variation in the minimum maintaining voltage was observed, that is, no problem was found in the life property. For the panels prepared in the comparative examples, the panel prepared in Comparative Example A3 had a firing voltage of 240 V and a minimum maintaining voltage of 175 V which were higher than those in the panel of the example of the present invention, necessitating a higher panel drive voltage. Regarding the life property, 30 min. after setting at the firing voltage, an increase in the minimum maintaining voltage was observed. For Comparative Example A4, the firing voltage was 160 V, the minimum maintaining voltage was

TABLE A4

Properties of various magnesium oxide films

| Sample | Form of fine particles | Average particle diameter | Adhesion | Film strength | Transparency | Crack | Film thickness |
| --- | --- | --- | --- | --- | --- | --- | --- |
| Ex. A1 | Particulate | 30 nm | Good | Good | Good | Free | 0.2 μm |
| Comp. Ex. A1 | — | — | Failure | Failure | Failure | — | — |
| Comp. Ex. A2 | — | — | Failure | Failure | Failure | — | — |
| Comp. Ex. A3 | Cubic | 800 nm | Good | Good | Failure | Free | 3.0 μm |
| Comp. Ex. A4 | Flaky | 200 nm | Good | Good | Good | Free | 0.5 μm |

In Comparative Examples A1 and A2, since the wetting property of each sol solution was poor, conditions such as coating speed were varied. However, a wet coating could not be evenly formed on the dielectric layer 5. This led to the evaluation results given in Table A4. For comparative Example A3, the film thickness was 3 μm, i.e., larger than that in the other comparative examples and the example, and the film was whitish and had poor transparency. Comparative Example A4 had no significant problem.

Then, for the opposed discharge alternating current type plasma displays except for those in Comparative Examples A1 and A2 wherein no protective layer could be formed, an alternating current pulse having a waveform of a drive frequency 15 kHz and a duty ratio of 23% was used to measure the firing voltage Vf and the minimum maintaining voltage Vsm.

After setting at the firing voltage, continuous discharge was performed for 60 min. Thereafter, the minimum main- 105 V, and no variation in the minimum maintaining voltage was observed, that is, no problem was found in the life property.

The results for the evaluation of the panel prepared in the example of the present invention, in comparison with the panels prepared in the other comparative examples, especially the panel prepared in Comparative Example A4 by vacuum deposition which had achieved satisfactory results in the prior art, show that the panel developed functions inherent in the magnesium oxide film and was satisfactory.

From the above results, it is apparent that the protective layer of a magnesium oxide film in the opposed discharge alternating current type plasma display prepared in the example of the present invention exhibits satisfactory properties in alternating current type plasma displays.

The use of the sol solution and the film forming method according to the present invention, for example, in the construction of an alternating current type plasma display, can provide a protective layer of a continuous film of magnesium oxide constituted by granular particles having a particle diameter in the range of from 5 to 100 nm. Therefore, the protective layer has high transparency, and the thickness of the protective layer can be reduced. Further, since the film strength is high, there is no fear of the dielectric layer being exposed by cracking. Therefore, a lowering in drive voltage can be accelerated, enabling a reduction in cost of drive circuit, which in turn leads to a reduction in cost of the body of the plasma display.

Further, since the protective layer can be formed by coating a sol solution, the film can be formed in a larger area at a lower cost as compared with film formation using a thin film process, realizing the production of a plasma display having a large area (for example, about 40 in. in terms of diagonal distance) at a low cost.

Furthermore, in the sol solution according to the present invention, since an organic compound having at least one hydroxyl group or an organic solvent containing at least one compound of the above type is used as the solvent, the sol solution is stable for a long period of time without causing agglomeration of fine particles of a double hydroxide of magnesium. Therefore, a magnesium oxide film prepared by coating the sol solution and sintering the coating is constituted by refined particles, improving the transparency of the resultant protective layer.

Further, according to the film forming method of the present invention, since an organic solvent is used as the solvent for the sol solution, upon sintering, no organic matter is left as a residue in the magnesium oxide film, realizing the preparation of a protective layer constituting of pure magnesium oxide.

In general, when the thickness of the protective layer in an alternating current type plasma display is thick, for example, as thickness as about 10 $\mu$m, the wall charge effect, a source of memory function, which is one of the important properties of the alternating current type plasma display, is deteriorated, necessitating a higher drive voltage. Consequently, specifications for transistors used in the drive circuit should cope with the use of high voltage. For this reason, the formation of a protective layer having a thickness of not more than 2 $\mu$m is the most important necessary and sufficient condition from the practical viewpoint. According to the present invention, the protective layer having a thickness of not more than 2 $\mu$m can be satisfactorily formed.

EXAMPLE B1

An opposed discharge alternating current type plasma display shown in FIG. 2 was prepared as follows. A 0.2 $\mu$m-thick electrode X 4a as a chromium electrode was vacuum-deposited on a front substrate 1 made of glass. A 0.8 $\mu$m-thick dielectric layer 5 was then vacuum-deposited, and a sol solution specified in Table B2 was used to form a 0.2 $\mu$m-thick protective layer 6 of a magnesium oxide film on the dielectric layer 5. Thereafter, a 150 $\mu$m-thick barrier 8 was formed on the protective layer 6 by screen printing, and a fluorescent material was coated on the barrier 8 to form a 10 $\mu$m-thick phosphor layer 9.

Separately, a chromium electrode was vacuum-deposited on a back substrate 2 made of glass and patterned to form an electrode Y 4b, and a dielectric layer 5 was vacuum-deposited on the electrode Y 4b. Thereafter, a 0.2 $\mu$m-thick protective layer 6 of a magnesium oxide film was formed in the same manner as described above in connection with the magnesium oxide film. The film thickness of the chromium electrode (electrode Y 4b) on the back substrate 2 was 0.2 $\mu$m, and the film thickness of the dielectric layer 5 was 0.8 $\mu$m.

Both the substrates thus obtained were laminated to each other so that the protective layers faced each other. 500 Torr of He—Xe (1.1%) Penning gas was sealed into a space defined by the barrier 8 to prepare an opposed discharge alternating current type plasma display of the present invention.

COMPARATIVE EXAMPLE B1

An attempt to prepare an opposed discharge alternating current type plasma display was made in the same manner as in the above example B1, except that, in the preparation of the sol solution, agglomerates of fine particles of magnesium hydroxide were dispersed in pure water instead of ethanol.

COMPARATIVE EXAMPLE B2

An opposed discharge alternating current type plasma display was prepared in the same manner as in the above example B1, except that a paste of magnesium oxide was coated by screen printing to form the protective layer 6 of a magnesium oxide film. The paste of magnesium oxide was prepared by dispersing a magnesium oxide powder having an average primary particle diameter of 0.18 to 0.25 $\mu$m (UBE 2000A, manufactured by Ube Industries, Ltd.) in a Si-based binder (10 parts by weight of $SiO_2$) to a concentration of 26% by weight and modifying the viscosity to 7,000 cps/25° C.

Printing was performed under conditions of plate gap 2.3 mm, squeegee indentation 1 mm, scraper indentation 1 $\mu$m, screen mesh 400, and emulsion thickness 10 $\mu$m. sintering was performed under atmospheric pressure at a temperature of 580° C. for one hr.

COMPARATIVE EXAMPLE B3

An opposed discharge alternating current type plasma display was prepared in the same manner as in the above example B1, except that the protective layer 6 of a magnesium oxide film was formed by vacuum deposition. In the vacuum deposition, an electron beam depositing machine (EX-900-C16, manufactured by Ulvac Japan Limited) was used to form a film under conditions of substrate temperature 300° C. and film formation rate 0.5 nm/sec to a thickness of 0.5 $\mu$m.

Before paneling, the alternating current type plasma displays (hereinafter referred to as "panels") prepared in the example and the comparative examples were evaluated for the properties of the magnesium oxide film constituting the protective layer. The results are summarized in Table B4. The adhesion and the film strength given in the table were evaluated by a scratch tester and a pencil hardness test. The transparency and the crack were visually inspected. The film thickness was measured with a profilometer ($\alpha$Step 300, manufactured by Tencor Instruments Japan Co., Ltd.).

TABLE B4

Properties of various magnesium oxide films

| Sample | Form of fine particles | Average particle diameter | Adhesion | Film strength | Transparency | Crack | Film thickness |
|---|---|---|---|---|---|---|---|
| Ex. B1 | Particulate | 30 nm | Good | Good | Good | Free | 0.2 μm |
| Comp. Ex. B1 | — | — | Failure | Failure | Failure | — | — |
| Comp. Ex. B2 | Cubic | 800 nm | Good | Good | Failure | Free | 3.0 μm |
| Comp. Ex. B3 | Flaky | 200 nm | Good | Good | Good | Free | 0.5 μm |

In Comparative Examples B1, since the wetting property of sol solution was poor, conditions such as coating speed were varied. However, a wet coating could not be evenly formed on the dielectric layer 5. This led to the evaluation results given in Table B4. For comparative Example B2, the film thickness was 3 μm, i.e., larger than that in the other comparative examples and the example, and the film was whitish and had poor transparency. Comparative Example B3 had no significant problem.

Then, for the opposed discharge alternating current type plasma displays except for those in Comparative Examples B1 wherein no protective layer could be formed, an alternating current pulse having a waveform of a drive frequency 15 kHz and a duty ratio of 23% was used to measure the firing voltage Vf and the minimum maintaining voltage Vsm.

After setting at the firing voltage, continuous discharge was performed for 60 min. Thereafter, the minimum maintaining voltage was measured and compared with the initial minimum maintaining voltage to investigate a change in voltage with the elapse of time. Thus, the life property of the panels was evaluated. The results are summarized in Table B5.

TABLE B5

PDP properties of various magnesium oxide films

| Sample | Firing voltage | Minimum maintaining voltage | Life |
|---|---|---|---|
| Ex. B1 | 155 V | 110 V | Good |
| Comp. Ex. B2 | 240 V | 175 V | Somewhat poor |
| Comp. Ex. B3 | 160 V | 105 V | Good |

As is apparent from Table B5, for the panel prepared in the example of the present invention, the firing voltage was 155 V, the minimum maintaining voltage was 110 V, and no variation in the minimum maintaining voltage was observed, that is, no problem was found in the life property. For the panels prepared in the comparative examples, the panel prepared in Comparative Example B2 had a firing voltage of 240 V and a minimum maintaining voltage of 175 V which were higher than those in the panel of the example of the present invention, necessitating a higher panel drive voltage. Regarding the life property, 30 min. after setting at the firing voltage, an increase in the minimum maintaining voltage was observed. For Comparative Example B3, the firing voltage was 160 V, the minimum maintaining voltage was 105 V, and no variation in the minimum maintaining voltage was observed, that is, no problem was found in the life property.

The results for the evaluation of the panel prepared in the example of the present invention, in comparison with the panels prepared in the other comparative examples, especially the panel prepared in Comparative Example B3 by vacuum deposition which had achieved satisfactory results in the prior art, show that the panel developed functions inherent in the magnesium oxide film and was satisfactory.

From the above results, it is apparent that the protective layer of a magnesium oxide film in the opposed discharge alternating current type plasma display prepared in the example of the present invention exhibits satisfactory properties in opposed discharge alternating current type plasma displays.

The use of the sol solution and the film forming method according to the present invention, for example, in the construction of an alternating current type plasma display, can provide a protective layer of a continuous film of magnesium oxide constituted by granular particles having a particle diameter of not more than 100 nm. Therefore, the protective layer has high transparency, and the thickness of the protective layer can be reduced. Further, since the film strength is high, there is no fear of the dielectric layer being exposed by cracking. Therefore, a lowering in drive voltage can be accelerated, enabling a reduction in cost of drive circuit, which in turn leads to a reduction in cost of the body of the plasma display.

Further, since the protective layer can be formed by coating a sol solution, the film can be formed in a larger area at a lower cost as compared with film formation using a thin film process, realizing the production of a plasma display having a large area (for example, about 40 in. in terms of diagonal distance) at a low cost.

Furthermore, in the sol solution according to the present invention, since an organic compound having at least one hydroxyl group or an organic solvent containing at least one compound of the above type is used as the solvent, the fine particles of magnesium hydroxide are less likely to agglomerate, offering a sol solution with fine particles of magnesium hydroxide stably dispersed for a long period of time. Therefore, a magnesium oxide film prepared by coating the sol solution and sintering the coating is constituted by refined particles, improving the transparency of the resultant protective layer.

Further, according to the film forming method of the present invention, since an organic solvent is used as the solvent for the sol solution, upon sintering, no organic matter is left as a residue in the magnesium oxide film, realizing the preparation of a protective layer constituting of pure magnesium oxide.

In general, when the thickness of the protective layer in an alternating current type plasma display is thick, for example, as thickness as about 10 μm, the wall charge effect, a source of memory function, which is one of the important properties of the alternating current type plasma display, is deteriorated, necessitating a higher drive voltage.

Consequently, specifications for transistors used in the drive circuit should cope with the use of high voltage. For this reason, the formation of a protective layer having a thickness of not more than 2 μm is the most important necessary and sufficient condition from the practical viewpoint. The sol solution and the method for film formation according to the present invention, the protective layer having a thickness of not more than 2 μm can be satisfactorily formed.

EXAMPLE C1 (Preparation of sol solution)
(1) Dehydration of Magnesium Acetate Tetrahydrate A commercially available magnesium acetate tetrahydrate was dried at 120° C. for 5 hr. in a vacuum dryer to prepare anhydrous magnesium acetate from which the hydrate had been completely removed.
(2) Preparation of Sol Solution Containing Dispersed Colloidal Particles of Magnesium Acetate 3 parts of the anhydrous magnesium acetate particles was added to an aqueous solution of 0.1 part of hydroxypropylmethyl cellulose in 97 parts of water, and the mixture was stirred at room temperature for 3 hr.

In the resultant sol solution with colloidal particles of magnesium acetate dispersed in water, the diameter of the colloidal particles was 120 nm. The sol solution was allowed to stand at room temperature for one month. As a result, it was stable, and settling of magnesium acetate was not observed.

EXAMPLE C2 (Formation of protective layer on alternating current type PDP)

The formation of a protective layer, for an alternating current type PDP, using the sol solution prepared in Example C1, applied to a display (a panel), of a color television will be described. Embodiments of the construction of such a panel are shown in FIGS. 1 and 2.

As shown in FIG. 1 (plane discharge system), the display comprises a front substrate 1 and a back substrate 2 disposed opposite to each other with a gas discharge space 3 sandwiched between these two substrates. The substrates 1 and 2 are formed of a glass plate having a predetermined thickness. A pair of electrodes 4 of an electrode X 4a and an electrode Y 4b are provided on the substrate 1 in its side facing the substrate 2, and a dielectric layer 5 is formed on the substrate 1 so as to cover the electrodes. The dielectric layer 5 is covered with a protective layer 6. In general, the thickness of the protective layer 6 should be not more than 2 μm. An address electrode 7 is formed on the substrate 2 in its side facing the substrate 1, and a phosphor is provided on the address electrode.

FIG. 2 shows another embodiment (counter electrode system) of the construction of the panel. In this embodiment, an electrode X 4a is formed on a front substrate 1 in its side facing a back substrate 2, the electrode X 4a is covered with a dielectric layer 5, and the dielectric layer 5 is covered with a protective layer 6. On the other hand, an electrode Y 4b, a dielectric layer 5, a protective layer 6, and a barrier 8 and a phosphor 9 are provided on the substrate 2 in its side facing the substrate 1.

The protective layer 6 in the FIGS. 1 and 2 was formed as follows.

The sol solution prepared in Example 1 was coated on the surface of the dielectric layer 5 by dip coating, a kind of coating printing, to a thickness of 2 μm in terms of thickness after drying in the air. After the formation of the coating, the coating was dried at 120° C. for one hr. and then heat-treated (sintered) at 500° C. for 2 hr. It was further baked to evaporate water as water vapor.

The resultant magnesium oxide film was completely transparent and firmly adhered the dielectric layer. Observation of the magnesium oxide film under a scanning electron microscope has revealed that particles in the surface of the magnesium oxide film are even and fine and constitute a dense film and the film thickness was not more than 2 μm.

COMPARATIVE EXAMPLE C1

A protective film of magnesium oxide was formed in the same manner as in Example C2, except that aqueous ammonia was added to an aqueous solution of magnesium acetate tetrahydrate and a protective film of magnesium oxide was formed using a liquid containing colloidal particles of magnesium hydroxide produced by hydrolysis. The magnesium oxide film thus formed had uniformity much inferior to the film formed in Example C2 and unsatisfactory adhesion to the dielectric layer.

According to the present invention, for example, it is possible to form a magnesium oxide-containing layer, with a thickness of not more than 2 μm, having excellent adhesion, to a substrate, such as a dielectric layer, which has been unattainable by the use of a printing paste used in the prior art for the formation of a magnesium oxide-containing layer, enabling the production of an alternating current type PDP having low firing voltage and drive voltage (voltage consumption).

Further, according to the present invention, since a coating method may be used, a film, such as a protective layer, having a large area can be formed at a low cost, realizing the production of a display for a large color television (for example, 40 in. in terms of diagonal distance).

What is claimed is:

1. An alternating current type plasma display comprising: a back substrate and a front substrate disposed opposite to each other; a gas discharge space sandwiched between the front and back substrates; a pair of electrodes provided on at least one of the substrates and covered with a dielectric layer; and a protective layer provided on the dielectric layer, the protective layer being constituted by a continuous film formed of fine particles of magnesium oxide having a diameter of 5 to 100 nm.

* * * * *